United States Patent [19]

Mehl

[11] Patent Number: 5,364,394

[45] Date of Patent: Nov. 15, 1994

[54] METHOD OF REMOVING HAIR FROM THE BODY AND INHIBITING FUTURE GROWTH

[76] Inventor: Thomas L. Mehl, 1015 Rte. 1 Hwy. 337, P.O. Box 1019, Newberry, Fla. 32669

[21] Appl. No.: 140,336

[22] Filed: Oct. 21, 1993

Related U.S. Application Data

[63] Continuation of Ser. No. 917,662, Jul. 20, 1992, abandoned, which is a continuation of Ser. No. 794,364, Nov. 13, 1991, abandoned, which is a continuation of Ser. No. 454,622, Dec. 21, 1989, abandoned.

[51] Int. Cl.$^5$ ............................................. A61B 17/41
[52] U.S. Cl. .......................................... 606/36; 606/43
[58] Field of Search .................................. 606/36, 43

[56] References Cited

U.S. PATENT DOCUMENTS

| 4,174,714 | 11/1979 | Mehl | 606/43 |
| 4,498,474 | 2/1985 | Chalmers et al. | 606/36 |

FOREIGN PATENT DOCUMENTS

| 1059489 | 5/1976 | Japan | 128/803 |

Primary Examiner—Lee S. Cohen
Attorney, Agent, or Firm—Shlesinger Arkwright & Garvey

[57] ABSTRACT

Hair is removed from the body and future growth is inhibited by treating the outer surface of the hair so as to reduce RF energy dissipation and permit more RF energy to reach the hair root and thereby damage or destroy the same. The hair is treated with a conductive material such as a conductive metal, a conductive solution such as a metal salt, an acid, or a base.

22 Claims, 2 Drawing Sheets

METHOD OF REMOVING HAIR FROM THE BODY AND INHIBITING FUTURE GROWTH

This application is a continuation, of application Ser. No. 07/917,662, filed on Jul. 20, 1992, now abandoned, which is a continuation of application Ser. No. 07/794,364, filed Nov. 13, 1991, now abandoned, which is a continuation of application Ser. No. 07/454,622, filed Dec. 21, 1989, now abandoned, entitled METHOD OF REMOVING HAIR FROM THE BODY AND INHIBITING FUTURE GROWTH.

BACKGROUND OF THE INVENTION

This invention relates to a radio frequency hair removal method which more effectively and permanently impairs future hair regrowth.

The most recent and more popular type of hair removal or epilator devices currently in use are tweezer type units through which RF energy is applied to the hair shaft. Typical of such devices and methods for removal of hair are described in Mehl U.S. Pat. Nos. 4,174,713; 4,566,454; and Mehl Pending application Ser. No. 372,852, filed Jun. 29, 1989. The methods taught in the above mentioned patents and application require in many instances thirty seconds treatment of each hair to be removed. Thus, removal of a substantial amount of hair is a time consuming though very effective process. With the present developments available., sufficient time is required in order to effectively damage the root system of the hair so that the hair may be removed by a very gentle upward lift rather than a sharp tug which would be normally applied for the removal of a single hair by a tweezers without any treatment of the hair. The present Mehl system is designed to avoid any discomfort to the person being treated for hair removal. Early developments in the removal of hair using RF energy require the use of a needle in combination with a tweezer such as described in U.S. Pat. Nos. 3,054,405; 2,894,512; and 853,096. The drawback of these devices is that the insertion of the needle under the skin produces irritation and swelling and burning of the tissues.

Other devices which do not use the needle but grip the hair a considerable distance from the skin and apply HF energy are illustrated in U.S. Pat. Nos. 2,888,927; 2,417,530; and 1,071,978. In these patents no requirement for insertion of the needle into the skin is made. However, these devices require a great deal of time for hair removal and do not effectively impair the development of the hair regrowth, and further, in many cases cause severe skin burns if the tweezer tip is brought in contact with the skin surface.

OBJECTS AND SUMMARY OF INVENTION

It is an object of this invention to provide a method for removing hair more effectively using RF energy by treating the hair to make the hair more conductive and thereby reduce the time necessary to sufficiently damage the root of the hair to cause it to release the hair from the body so that it may be removed by a mere gentle force rather than a tug.

Another object of this invention is to cut the present treatment time for each hair when using RF energy from as much as one-half to one-quarter or even less of the amount of time presently needed to effectively remove the hair.

Yet another object of this invention is to provide a method for removing the hair in which the hair is pretreated prior to the application of RF energy to make it more receptive to the RF energy and to reduce dissipation of the RF energy prior to its reaching the root of the hair.

A further object of this invention is provide a method of pretreating the hair prior to the application of RF energy which is inexpensive and does not require specialized training for the individual utilizing the method.

Still a further object of this invention is to provide a method for removing hair which can be applied to all of the hair to be removed at one time prior to the application of RF energy.

Another object of this invention is to provide a method for treating the hair which will permit the use of existing RF energy hair removal devices without requiring modification of the same.

Still a further object of this invention is to provide a method of removing hair which does not require the hair to be trimmed prior to the application of RF energy as was required in the past.

A further object of this invention is to provide a method for removing hair which will not cause discomfort to the individual and will not burn the outer tissues of the skin and cause discomfort to the person who's hair is being removed.

Another object of this invention is to provide a shorter path for the RF energy through the hair from the external surface by reducing the thickness of the cuticle of the hair by the treatment of the hair cuticle prior to application of the RF hair grasping device.

In summary, this invention provides a new method for the very rapid removal of hair through the use of RF energy by treatment of the hair prior to the application of RF energy.

These and other objects and features of this invention will be apparent from the following description and claims.

DESCRIPTION OF THE INVENTION

Figure 1:
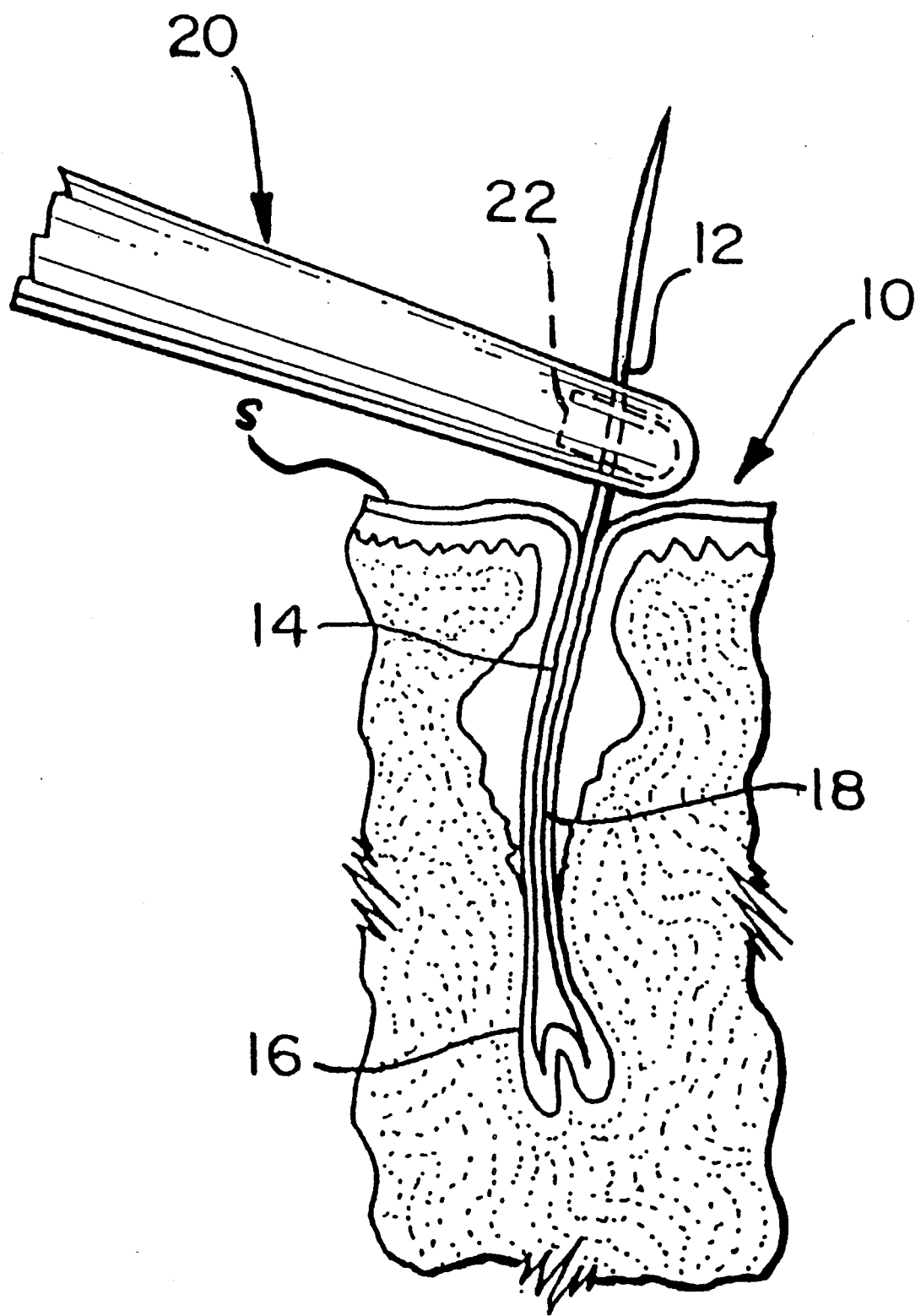
FIG. 1 is a fragmentary cross-sectional view of a hair in position within a tissue and showing it held between engaging ends of an Radio Frequency (RF) tweezer.
Figure 2:
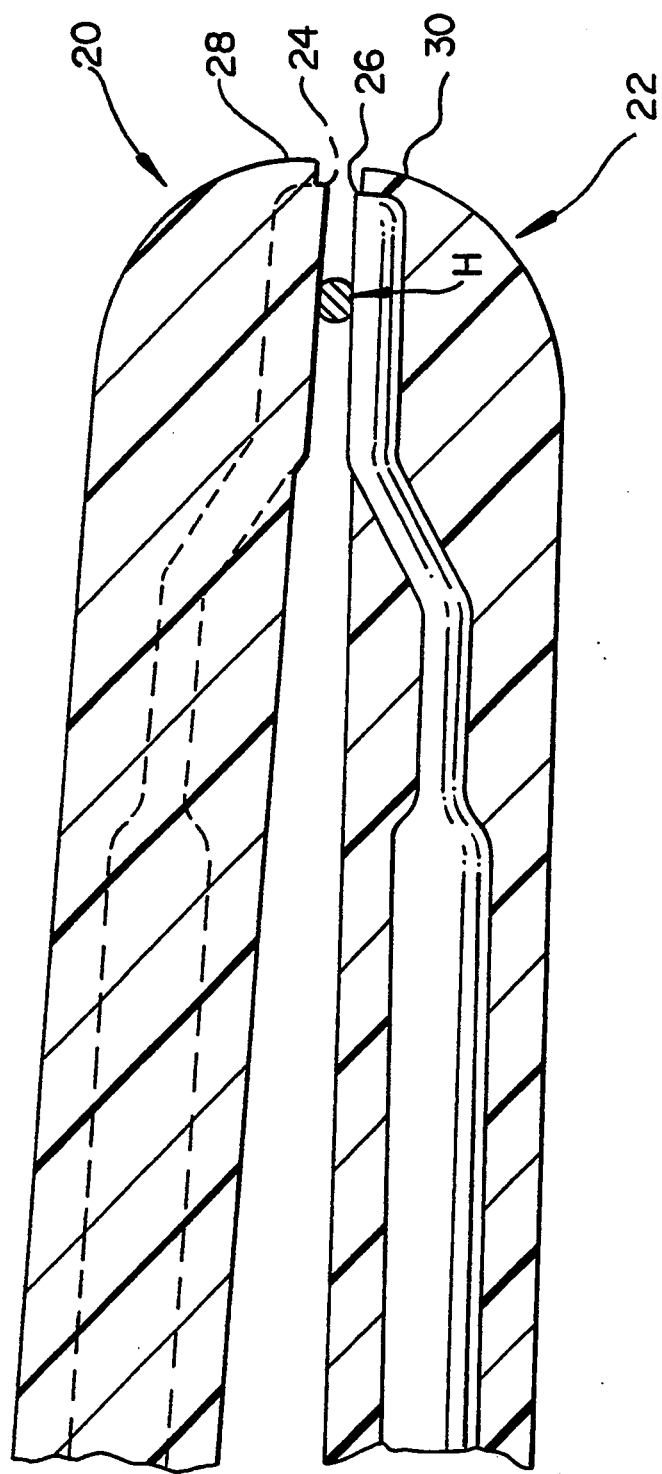
FIG. 2 is a fragmentary cross-sectional view of the tweezers shown in FIG. 1 with the tips engaging a hair shaft.

Referring particularly to both FIGS. 1 and 2, a section of the tissue containing a hair is generally indicated at 10 with the external portion of the hair 12 extending upwardly from the skin surface S, while the internal portion of the hair shaft 14 extends downwardly to the hair follicle 16. The hair has a central core section 18 which conducts radio frequency energy (RF) along the length of the hair shaft portions 12 and 14 to the follicle 16 by way of the central core section 18.

The external section of the hair shaft 12 is shown grasped between two opposed tweezer arm ends 20 and 22. The two opposed tweezer arm ends 20 and 22 are similar in construction and may carry opposed metal RF frequency conducting tweezer pads 24 and 26 which act as hair engaging surfaces. As illustrated in FIG. 2, pad 24 is shown in phantom lines to indicate that pad 24 may be deleted as only one RF energy pad such as 26 may be required. Thus, the tweezer arm 22 would have a plastic extending area to fill the void of the unnecessary pad 24. The hair shaft H is shown in FIG. 2 grasped between the pads 24 and 26. Dielectric Insulation 28 and 30 surrounds the hair engaging surfaces of the pads 24 and 26 to provide RF insulation and focussing, and also to prevent burning the skin when applying RF energy. Further details of the tweezer are shown in the Mehl patents and application referred to above.

It is to be noted in FIG. 1 that the hair shaft extends beyond the tweezers normally and with the method of this invention need not be cut down as previously noted in the aforementioned patents and application.

As has been noted above, the method of removing the hair from the body described in this invention requires a pretreatment of the hair prior to the application of the RF energy. It has been found that treating the hair with an RF conductive material produces substantially improved results in both time required to gently remove the hair as well as more effective destruction of hair root.

Hair by its very nature contains a certain amount of natural oils as well as accumulated dust and dirt. Sunlight and oxygen acting on the hair also effect the surface of the hair and all of these aspects impede the RF energy going to the hair core and thence to the hair root.

One method of treating the hair is the removal of at least a portion of the cuticle or hard outer surface of the hair by abrading the hair either chemically by etching or mechanically by sanding or the like. The abrading away of the cuticle, reduces the diameter of the hair and thus reduces the distance the RF energy must travel. Softening of the cuticle also allows for hair deformation, which also reduces the diameter when the tweezers grasp the hair, since the tweezers make indentation in the hair when pressure is applied. A softening compound such as a typical hair wave or straightening solution well known in the market including those having a thioglycollate of ammonium, potassium or sodium may be used.

It has been found that treatment of the hair with an electrically conductive material many fold increases the effects of the RF energy applied to the hair and hastens the destruction of the hair root and the release of the hair so that it can be gently removed without tugging as in the case of normal plucking of a hair from the body without the application of RF energy.

The treatment requires the application of an RF energy conductive material such as a metal or a conductive non-metal including solids, viscous materials, liquids and the like. Water soluble inorganic and organic salts, acids, and the bases may be used so long as they are weak and will not damage the skin tissue. A 0.5% to 1.5% water solution of a soluble salt acid or base has been found effective with conductive acids salts and bases. Standard chemistry books will indicate the conductivity of various acids, bases and salts whether inorganic or organic. A 1% solution of salts such as gold chloride, silver chloride, copper chloride, and the like as well as 1% solutions of acids, such as acidic, citric, oxalic, and lactic are also effective. 1% solutions of ammonium hydroxide, and other conductive bases may be used. Conductive ointments or salves such as used by physicians in cardiology in EKG equipment and the like which are conductive and available on the market may also be used. The application of conductive metal powders may also be used to treat the hair although they are more difficult to use than solutions such as described above.

Upon the application of the conductive material to the hair, the cuticle or outer hard portion of the hair which is somewhat porous, picks up the material and provides for more rapid conduction of the RF energy directly to the core and thence to the hair root for destruction and damage to the same.

In addition, it has been found that initial washing of the hair by standard means such as soap and water tends to remove a good deal of the oils in the hair and make the hair more supple and receptive to the conductive material to be applied. The washing opens the pores of the hair significantly as well as cleans the hair. Steaming of the hair prior to the application of the conductive material also aids in the opening up of the pores of the hair to make the hair more receptive to the conductive material being applied.

In test conducted, it has been found that the treatment of the hair by a 1% conductive solution of silver chloride or silver nitrate, copper chloride, or copper sulfate, even though not washed reduces the treatment period of the hair by the RF from 20 to 30 seconds to from 3 to 7 seconds and in most instances averages about 5 seconds per hair. This inventions shows dramatic improvement over present existing systems and results in substantial reductions in cost of treatment as well as in the time required. The cost for the solutions are minimal as compared with the time required for application of the RF energy in order to remove a single hair.

The technician using this method will preferably wash or steam the hair prior to the application of the conductive material to the hair. The application of the conductive material to the hair can be done in a number different ways such as washing the area to be treated with a cloth by applying several strokes to the hair to be sure that the solution has effectively been retained by the hair. Sponging, massaging and dampening or wetting the hair should require no more than 5 to 10 seconds application to the hair in order to obtain effective distribution of the conductive material on the hair.

Once the hair has been treated with the conductive material, the RF energy is applied by means of tweezers or the like to the hair. A gentle lifting upward of the tweezers within from 3 to 7 seconds will show effective removal of the hair with the gentle upward motion without tugging of the same. The average time for treatment is about 5 seconds.

It has been known that different types of hair and hair colors have required more or less RF energy to permit removal of the hair and inhibit future growth. Treatment of the hair with a conductive material has shown to be substantially equally effective on all types of hair as to the time required for removal thereof.

While this invention has been described as having a preferred method, it is understood that it is capable of further modifications, uses and/or adaptations of the invention and following in general the principles of the invention and including such departures from the prevent disclosure as come within known or customary practice in the art to which the present invention pertains, and as may be applied to essential features hereinbefore set forth, and fall within the scope of the invention or the limits of the claims appended hereto.

What is claimed is:

1. The method of removing a hair from a skin surface of an individual and inhibiting future growth by causing said hair to be sufficiently damaged at its root so as to be more readily releasable at its root and removable by a very gentle force rather than the normal force required to pluck a non-treated hair from the skin surface, comprising the steps of:
  a) treating the outer surface of the hair which has a longitudinally extending inner central core to reduce RF resistance between the outer hair surface and said inner central core of the hair to permit more RF energy during an entire treatment time to enter the inner central core and travel therealong within the hair interior to reach the hair root;
  b) firmly grasping the hair between a pair of opposed RF insulated hair engaging surfaces at a point relatively close to but clear of and above the skin surface of the grasped hair;
  c) applying RF energy to at least said one of said hair engaging surfaces;
  d) holding said hair engaging surfaces in firm engagement with said hair while applying focussed RF energy to said hair for a period of time sufficient to cause the RF energy to travel across the hair and into the inner core of the hair and to damage the hair root sufficiently to permit the hair to be removed by a very gentle upward lift;
  e) applying a gentle upward lift to the hair by the hair engaging surfaces during application of said RF energy, without exerting the tug ordinarily required for removal of non-treated hair.

2. The method of claim 1 and wherein:
  a) the treatment of the outer surface of the hair includes impregnating the outer surface of the hair with an RF energy conductive material.

3. The method of claim 2 and including the step of:
  a) using RF energy conductive material in the form of a liquid.

4. The method of claim 3 and including the step of:
  a) using RF energy conductive liquid in the form of a hydrolytic compound taken from the group consisting of:
    1) water soluble inorganic and organic salts;
    2) water soluble inorganic and organic acids; and
    3) water soluble inorganic and organic bases.

5. The method of claim 4 and including the step of:
  a) using said water soluble salts, acids and bases in a water solution of from about 0.5% to saturation.

6. The method of claim 3 and including the step of:
  a) using RF liquid in the form of a salt taken from the group consisting of gold, silver, copper and platinum.

7. The method of claim 2 and including the step of:
  a) using RF energy conductive material in the form of a viscous material.

8. The method of claim 2 and including the step of:
  a) using RF energy conductive material in the form of a hydrolytic material.

9. The method of claim 2 and including the step of:
  a) washing the hair prior to impregnating the outer surface of the hair with an RF conductive material.

10. The method of claim 2 and including the step of:
  a) steaming the hair prior to impregnating the outer surface of the hair with an RF conductive material.

11. The method of claim 2 and including the step of:
  a) treating the outer surface of the hair by metabolizing in the body of the individual a metallic compound to increase overall hair conductivity during hair growth.

12. The method of claim 1 and wherein:
  a) the treatment of the outer surface of the hair includes abrading.

13. The method of claim 12 and wherein:
  a) the abrading step is chemical abrading.

14. The method of claim 12 and wherein:
  a) the abrading step is mechanical abrading.

15. The method of claim 14 and wherein:
  a) the mechanical abrading step is sanding.

16. The method of claim 1 and including the step of:
  a) applying said RF energy for a period of not less than about 2½ seconds and not exceeding about 7½ seconds.

17. The method of claim 16 and wherein:
  a) said time period is about 5 seconds.

18. The method of claim 1 and including the step of:
  a) maintaining a dielectric between the RF energy insulated hair engaging surfaces and the skin surface at all times during the application of RF energy to the hair.

19. The method of removing hair from a skin surface of the body of an individual and inhibiting future growth to cause said hair to be sufficiently damaged at its root so as to be releasable at its root and removed by a very gentle force rather than normal force required to pluck a non-treated hair from the body, comprising the steps of:
  a) treating the cuticle of a hair having a longitudinally extending inner central core to cause the hair to absorb an RF energy conductive material to thereby reduce RF resistance between the outer surface and the inner central core of the hair during an entire period of RF application and to thereby reduce RF energy losses and permit more RF energy to travel down the core to reach the hair root;
  b) firmly grasping the hair between a pair of opposed RF insulated hair engaging surfaces at a point relatively close to but clear of and above the skin surface, at least one of the hair engaging surfaces being capable of emitting focussed RF energy to said grasped hair;
  c) applying RF energy to at least one of said hair engaging surfaces;
  d) holding said hair engaging surfaces in firm engagement with said hair while applying RF energy to said hair for a period of time sufficient to cause the RF energy to travel into the inner core of said hair and along the core to said hair root to cause said hair at said root to be damaged sufficiently to inhibit future growth;
  e) sensing when there is sufficient damage to said hair root to permit ready release of said hair from said skin surface by applying a gentle upward pull by said hair engaging surfaces away from said skin surface during application of said RF energy without requiring the normal tug required to pull a nontreated hair; and,
  f) completely removing said treated hair from said skin surface by continuing the gentle upward movement away from said skin surface by said hair engaging surfaces.

20. The method of claim 19 and including the step of:
  a) applying said RF energy for a period of not less than about 2½ seconds and not exceeding about 7½ seconds.

21. The method of claim 19 and wherein:
  a) said time period is about 5 seconds.

22. The method of claim 19 and including the step of:
  a) maintaining a dielectric between the RF energy insulated hair engaging surfaces and the skin surface at all times during the application of RF energy to the hair.

* * * * *